(12) United States Patent
Dargazanli et al.

(10) Patent No.: US 7,776,880 B2
(45) Date of Patent: Aug. 17, 2010

(54) DERIVATIVES OF PYRROLIZINE, INDOLIZINE AND QUINOLIZINE, PREPARATION THEREOF AND THERAPEUTIC USE THEREOF

(75) Inventors: Gihad Dargazanli, Paris (FR); Genevieve Estenne-Bouhtou, Paris (FR); Florence Medaisko, Paris (FR); Maria-Carmen Renones, Paris (FR)

(73) Assignee: sanofi-aventis, Paris (FR)

( * ) Notice: Subject to any disclaimer, the term of this patent is extended or adjusted under 35 U.S.C. 154(b) by 5 days.

(21) Appl. No.: 12/407,276

(22) Filed: Mar. 19, 2009

(65) Prior Publication Data

US 2009/0258899 A1 Oct. 15, 2009

Related U.S. Application Data

(63) Continuation of application No. PCT/FR2007/001545, filed on Sep. 21, 2007.

(30) Foreign Application Priority Data

Sep. 22, 2006 (FR) .................................. 06 08348

(51) Int. Cl.
  A61K 31/44 (2006.01)
  A61K 31/40 (2006.01)
  C07D 307/93 (2006.01)
  C07D 455/02 (2006.01)
  C07D 221/02 (2006.01)

(52) U.S. Cl. ........................ 514/306; 514/413; 549/465; 546/138; 546/112

(58) Field of Classification Search .................. 546/191, 546/112, 138; 514/299, 413, 306; 549/465
See application file for complete search history.

(56) References Cited

U.S. PATENT DOCUMENTS

| | | | |
|---|---|---|---|
| 3,801,636 | A | 4/1974 | Horrom et al. |
| 4,409,225 | A | 10/1983 | Hadley |
| 5,552,398 | A | 9/1996 | King et al. |
| 7,288,656 | B2 | 10/2007 | Dargazanli et al. |
| 7,335,670 | B2 | 2/2008 | Dargazanli et al. |
| 2008/0070941 | A1 | 3/2008 | Dargazanli et al. |

FOREIGN PATENT DOCUMENTS

| | | |
|---|---|---|
| EP | 0556672 | 8/1993 |
| FR | 2861073 | 4/2005 |
| WO | WO 02/24695 A2 | 3/2002 |
| WO | WO 2005/037783 | 4/2005 |

OTHER PUBLICATIONS

West, Anthony R., Solid State Chemistry and its Applications, Wiley, New York, 1988, pp. 358 & 365.*

Agami et al, Synthesis of alpha-Substituted Allylic Amines via a Modified Bruylants Reaction, Organic Letters, 2000 (2) 14 pp. 2085-2088.
Cuny et al, Regioselective Olefin Hydroformylation as a Route to Indolizidine and Pyrrolizidine Alkaloids, Synlett., May 1995, pp. 519-522.
Dondoni et al, Stereoselective Addition of 2-Furyllithium and 2-Thiazolyllithium to Sugar Nitrones. Synthesis of Carbon-Linked Glycoglycines, J. Org. Chem., 1997 (62) pp. 5484-5496.
Hadley et al, Substituted Benzamides with conformationally Restricted Side Chains. 3. Azabicyclo[x.y.0.]Derivatives as Gastric Prokinetic Agents., Bioorganic & Med. Chem. Letters, 1992 (2) 9 pp. 1147-1152.
Hodgson et al, III. 3-Nitro-4-amino- and the 3:4-Dihalogenobenzaldehydes, J. Chem. Soc., 1927 (25) pp. 20-27.
Martinelli et al, Aromatic Chlorination of p-Aminobenzoic Acid Derivatives, Improved Syntheses of Mono- and Dichloromethotrexate, J. Org. Chem. 1980 (45) pp. 527-529.
Ohmomo et al, Synthesis and Evaluation of Iodinated Benzamide Derivatives as Selective and Reversible Monoamine Oxidase B Inhibitors, Chem. Pharm. Bull. 1992 (40) 7 pp. 1789-1792.
Polniaszek et al, Enantioselective Total Syntheses of Indolizidine Alkaloids (–)-205A and (–)-235B, J. Org. Chem., 1991 (56) pp. 4868-4874.
Polniaszek et al, Enantioselective Total Syntheses of Indolizidine Alkaloids 167B and 209D, J. Org. Chem., 1990 (50) pp. 4688-4693.
Stewart et al, Synthesis of Substituted 9-Oxo-9,10-dihydroacridine-4-carboxylic Acids. I. Factors Affecting the Direction of Ring Closure of Substituted N-(2-Carboxyphenylamino)benzoic Acids, Aust. J. Chem., 1984 (37) pp. 1939-1950.
Tayar et al, Interaction of neuroleptic drugs with rat striatal D-1 and D-2 dopamine receptors: a quantitative structure—affinity relationship study, Eur. J. Med. Chem., 1988 (23) pp. 173-182.
Wu et al, Room Temperature Stable 3-Lithiothiophene: a Facile Synthesis of 3-Functional Thiophenes, Tetrahedron Letters 1994 (35) 22 pp. 3673-3674.

* cited by examiner

Primary Examiner—Janet L Andres
Assistant Examiner—Binta M Robinson
(74) Attorney, Agent, or Firm—Kelly L. Bender

(57) ABSTRACT

The disclosure relates to a compound of formula (I):

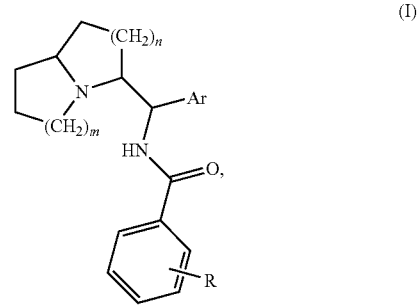

wherein m, n, Ar, and R are as defined in the disclosure, to compositions containing them and to their therapeutic use. The disclosure also relates to processes for preparing these compounds and to certain intermediate compounds.

14 Claims, No Drawings

DERIVATIVES OF PYRROLIZINE, INDOLIZINE AND QUINOLIZINE, PREPARATION THEREOF AND THERAPEUTIC USE THEREOF

CROSS REFERENCE TO RELATED APPLICATIONS

This application is a continuation of International application No. PCT/FR2007/001545, filed Sep. 21, 2007, which is incorporated herein by reference in its entirety; which claims the benefit of priority of French Patent Application No. 0608348, filed Sep. 22, 2006.

A subject-matter of the present invention is pyrrolizine, indolizine and quinolizine derivatives, their preparation and their therapeutic application.

SUMMARY OF THE INVENTION

The compounds of the invention correspond to the general formula (I)

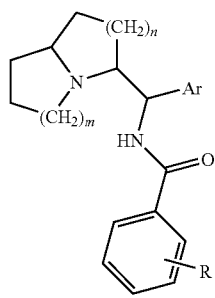

in which:
m and n each represent, independently of one another, the number 1 or 2,
Ar represents a group chosen from the phenyl, naphth-1-yl, naphth-2-yl, pyridin-2-yl, pyridin-3-yl, pyridin-4-yl, furan-2-yl, furan-3-yl, thien-2-yl, thien-3-yl, thiazol-2-yl and oxazol-2-yl groups, it being possible for this group Ar optionally to be substituted by one or more substituents chosen from halogen atoms and $(C_1-C_6)$alkyl, $(C_3-C_7)$cycloalkyl, $(C_3-C_7)$cycloalkyl$(C_1-C_6)$alkyl, $(C_1-C_6)$alkoxy, $(C_3-C_7)$cycloalkyloxy, $(C_3-C_7)$cyclo-alkyl$(C_1-C_6)$alkyloxy, $(C_1-C_6)$alkylthio, $(C_3-C_7)$cycloalkylthio, $(C_3-C_7)$cycloalkyl-$(C_1-C_6)$alkylthio, mono- or polyfluoro$(C_1-C_6)$alkyl and mono- or polyfluoro$(C_1-C_6)$alkyloxy groups,
R represents either a hydrogen atom or one or more substituents, identical to or different from one another, chosen from halogen atoms and mono- or polyfluoro$(C_1-C_6)$alkyl and mono- or polyfluoro$(C_1-C_6)$alkyloxy, linear $(C_1-C_6)$alkyl, branched or cyclic $(C_3-C_7)$alkyl, $(C_3-C_7)$cycloalkyl$(C_1-C_6)$alkyl, $(C_1-C_6)$alkoxy, $(C_3-C_7)$cycloalkyloxy, $(C_3-C_7)$cycloalkyl $(C_1-C_6)$alkyloxy, $(C_1-C_6)$alkylthio, cyano, amino, phenyl, acetyl, benzoyl, $(C_1-C_6)$alkylsulphonyl, carboxyl, $(C_1-C_6)$alkoxycarbonyl and pentafluorosulphanyl groups.

DETAILED DESCRIPTION OF THE INVENTION

The compounds of general formula (I) have three asymmetric centers; they can exist in the form of enantiomers or of threo or erythro diastereoisomers with a cis or trans stereochemistry of the substituent of the bicycle, or as a mixture of such isomers. They can also exist in the form of free bases, of addition salts with acids and/or of solvates or of hydrates, namely in the form of combinations or associations with one or more molecules of water or with a solvent. Such hydrates and solvates also form part of the invention.

Among the compounds of the invention, a first group of compounds is composed of the compounds for which:
Ar represents a group chosen from the phenyl, pyridin-2-yl, pyridin-3-yl, pyridin-4-yl, thien-2-yl and thien-3-yl groups, it being possible for this group Ar optionally to be substituted by one or more substituents chosen from halogen atoms and $(C_1-C_6)$alkyl, $(C_3-C_7)$cycloalkyl, $(C_3-C_7)$cycloalkyl$(C_1-C_6)$alkyl, $(C_1-C_6)$alkoxy, $(C_3-C_7)$cycloalkyloxy, $(C_3-C_7)$cycloalkyl$(C_1-C_6)$alkyloxy, $(C_1-C_6)$alkylthio, $(C_3-C_7)$cycloalkylthio, $(C_3-C_7)$cyclo-alkyl$(C_1-C_6)$alkylthio, mono- or polyfluoro$(C_1-C_6)$alkyl and mono- or polyfluoro-$(C_1-C_6)$alkyloxy groups,
m, n and R being as defined above.

Among the compounds of the invention, a second group of compounds is composed of the compounds for which:
Ar represents a group chosen from the phenyl, pyridin-3-yl and thien-3-yl groups, it being possible for this group Ar optionally to be substituted by one or more substituents, identical to or different from one another, chosen from halogen atoms,
m, n and R being as defined above.

Among the compounds of the invention, a third group of compounds is composed of the compounds for which:
R represents either a hydrogen atom or one or more substituents, identical to or different from one another, chosen from halogen atoms and mono- or polyfluoro$(C_1-C_6)$alkyl, mono- or polyfluoro$(C_1-C_6)$alkyloxy, linear $(C_1-C_6)$alkyl and pentafluorosulphanyl groups,
m, n and Ar being as defined above.

Among the compounds of the invention, a fourth group of compounds is composed of the compounds for which:
m and n each represent, independently of one another, the number 1 or 2,
Ar represents a group chosen from the phenyl, pyridin-3-yl and thien-3-yl groups, it being possible for this group Ar optionally to be substituted by one or more halogen atoms,
R represents either a hydrogen atom or one or more substituents, identical to or different from one another, chosen from chlorine and the methyl, trifluoromethyl, trifluoromethoxy and pentafluorosulphanyl groups.

Among the compounds of the invention, a fifth group of compounds is composed of the following compounds:
trans-threo-2-Chloro-N-[(octahydroindolizin-5-yl)phenylmethyl]-3-trifluoromethyl-benzamide hydrochloride 1:1.
trans-erythro-2-Chloro-N-[(octahydroindolizin-5-yl)phenylmethyl]-3-trifluoromethyl-benzamide hydrochloride 1:1.
trans-threo-2,6-Dichloro-N-[(octahydroindolizin-5-yl)phenylmethyl]-3-trifluoromethyl-benzamide hydrochloride 1:1.
trans-erythro-2,6-Dichloro-N-[(octahydroindolizin-5-yl) phenylmethyl]-3-trifluoromethyl-benzamide hydrochloride 1:1.
trans-threo-2-Chloro-N-[(octahydroindolizin-3-yl)phenylmethyl]-3-trifluoromethyl-benzamide hydrochloride 1:1.
2-Chloro-N—[(S)-(3S,8aR)-(octahydroindolizin-3-yl)phenylmethyl]-3-trifluoromethyl-benzamide hydrochloride 1:1.
trans-threo-2-Methyl-N-[(octahydroindolizin-3-yl)phenylmethyl]-3-trifluoromethyl-benzamide hydrochloride 1:1.

cis-erythro-2-Methyl-N-[(octahydroindolizin-3-yl)phenyl-methyl]-3-trifluoromethyl-benzamide hydrochloride 1:1.

2-Chloro-N—[(S)-(3S,8aR)-(octahydroindolizin-3-yl)(pyridin-3-yl)methyl]-3-trifluoromethylbenzamide hydrochloride 1:1.

2-Chloro-N—[(S)-(3S,8aR)-(octahydroindolizin-3-yl)(thiophen-3-yl)methyl]-3-trifluoro-methylbenzamide hydrochloride 1:1.

cis-erythro-2-Chloro-N-[(octahydroindolizin-3-yl)phenylmethyl]-3-trifluoromethyl-benzamide hydrochloride 1:1.

2-Chloro-N—[(S)-(3R,8aR)-(octahydroindolizin-3-yl)(thiophen-3-yl)methyl]-3-trifluoro-methylbenzamide hydrochloride 1:1.

2-Chloro-N—[(S)-(3R,8aR)-(octahydroindolizin-3-yl)(pyridin-3-yl)methyl]-3-trifluoro-methylbenzamide hydrochloride 1:1.

trans-threo-2-Chloro-N-[(octahydroquinolizin-4-yl)phenylmethyl]-3-trifluoromethyl-benzamide hydrochloride 1:1.

trans-erythro-2-Chloro-N-[(octahydroquinolizin-4-yl)phenylmethyl]-5-trifluoromethyl-benzamide hydrochloride 1:1.

trans-threo-2,6-Dichloro-N-[(octahydroquinolizin-4-yl)phenylmethyl]-3-trifluoromethyl-benzamide hydrochloride 1:1.

trans-erythro-2,6-Dichloro-N-[(octahydroquinolizin-4-yl)phenylmethyl]-3-trifluoromethyl-benzamide hydrochloride 1:1.

trans-erythro-2-Methyl-N-[(octahydroquinolizin-4-yl)phenylmethyl]-3-trifluoromethyl-benzamide hydrochloride 1:1.

trans-threo-2,6-Dichloro-N-[(4-fluorophenyl)(octahydroquinolizin-4-yl)methyl]-3-trifluoromethylbenzamide hydrochloride 1:1.

trans-threo-2-Chloro-N-[(octahydroquinolizin-4-yl)(pyridin-3-yl)methyl]-3-trifluoromethyl-benzamide hydrochloride 1:1.

trans-erythro-2-Chloro-N-[(octahydroquinolizin-4-yl)phenylmethyl]-3-trifluoromethyl-benzamide hydrochloride 1:1.

trans-threo-2-Chloro-N-[(octahydroquinolizin-4-yl)phenylmethyl]-5-trifluoromethyl-benzamide hydrochloride 1:1.

trans-threo-2-Methyl-N-[(octahydroquinolizin-4-yl)phenylmethyl]-3-trifluoromethyl-benzamide hydrochloride 1:1.

trans-erythro-2-Chloro-N-[(octahydroquinolizin-4-yl)(thiophen-3-yl)methyl]-3-trifluoro-methylbenzamide hydrochloride 1:1.

trans-threo-2-Chloro-3-methyl-N-[(octahydroquinolizin-4-yl)phenylmethyl]benzamide hydrochloride 1:1.

trans-threo-2-Chloro-N-[(4-fluorophenyl)(octahydroquinolizin-4-yl)methyl]-3-trifluoro-methylbenzamide hydrochloride 1:1.

trans-erythro-2-Chloro-N-[(4-fluorophenyl)(octahydroquinolizin-4-yl)methyl]-3-trifluoro-methylbenzamide hydrochloride 1:1.

trans-threo-2-Chloro-3-methoxy-N-[(octahydroquinolizin-4-yl)phenylmethyl]benzamide hydrochloride 1:1.

trans-threo-N-[(Octahydroquinolizin-4-yl)phenylmethyl]-3-trifluoromethoxybenzamide hydrochloride 1:1.

trans-threo-N-[(Octahydroquinolizin-4-yl)phenylmethyl]-3-(pentafluorosulphanyl)-benzamide hydrochloride 1:1.

2-Chloro-N-[(hexahydropyrrolizin-3-yl)phenylmethyl]benzamide hydrochloride 1:1.

The compounds of general formula (I) can be prepared by a process illustrated by the following Scheme 1.

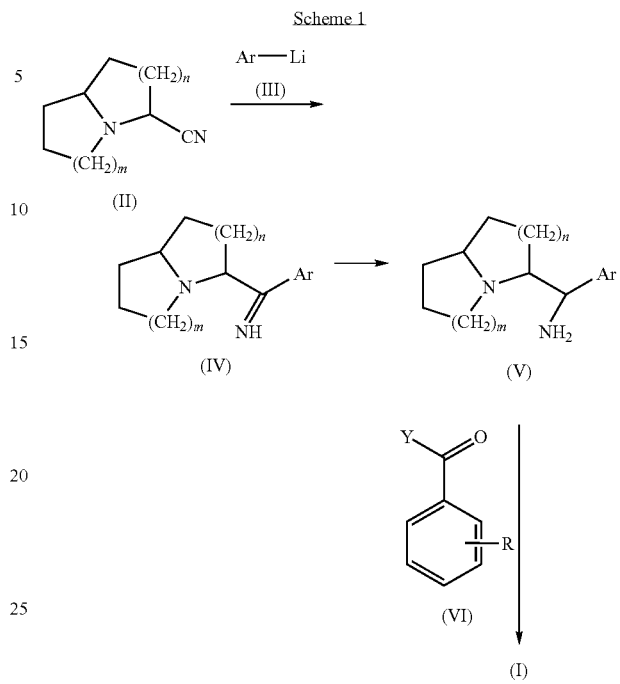

Scheme 1

A nitrile of general formula (II), in which m and n are as defined above, is reacted with a lithiated derivative of general formula (III), in which Ar is as defined above, in an ethereal solvent, such as diethyl ether or tetrahydrofuran, between −90° C. and −30° C.; an intermediate imine of general formula (IV) is obtained and is reduced to a primary amine of general formula (V) by a reducing agent, such as sodium borohydride, in a protic solvent, such as methanol, between 0° C. and ambient temperature. Amide coupling is subsequently carried out between the diamine of general formula (V) and an activated acid or an acid chloride of general formula (VI), in which Y represents an activated OH group or a chlorine atom and R is as defined above, using the methods known to a person skilled in the art, to arrive at the amide of general formula (I).

The compounds of general formula (II) with n=1 and m=2 have a cis and trans relative stereochemistry and they result respectively in the compounds of general formula (I) of cis-erythro and trans-threo stereochemistry.

The compounds of general formula (II) with n=2 and m=1 or n and m=2 have a trans relative stereochemistry and they result in the compounds of general formula (I) of trans-erythro and trans-threo stereochemistry.

Finally, the compound of general formula (II) with n and m=1 has a trans and cis relative stereochemistry and it results in the compounds of general formula (I) in the form of a mixture of isomers which can be separated by liquid chromatography.

Furthermore, the chiral compounds of general formula (I) can be obtained by separation of the racemic compounds by high performance liquid chromatography (HPLC) on a chiral column or by resolution of the racemic amine of general formula (V) by use of a chiral acid, such as tartaric acid, camphorsulphonic acid, dibenzoyltartaric acid or N-acetylleucine, by the fractional and preferential recrystallization of a diastereoisomeric salt in a solvent of alcohol type, or by enantioselective synthesis using a chiral nitrile of general formula (II).

The nitriles of general formula (II) are described in *Synlett*, (1995), 519-522, when n and m represent 1 with a cis and trans stereochemistry, in *J.O.C*, 55, (1990), 4688-4693 and *J.O.C.*, 56, (1991), 4868-4874, when n represents 2 and m represents 1 with a trans stereochemistry, and in *Org. Letters*, 2, (2000), 2085-2088, when n represents 1 and m represents 2 with a trans and cis stereochemistry, and, finally, they can be prepared according to methods analogous to those described above when n and m represent 2 with a trans stereochemistry in the racemic or chiral series. The lithiated derivatives of general formula (III) are available commercially or they can be prepared according to methods known to a person skilled in the art and analogous to those described in *J.O.C.*, 62, (1997), 5484-5496 and *Tetrahedron Letters*, 35, (1994), 3673-3674.

Certain acids and acid chlorides of general formula (VI) are available commercially or can be obtained according to methods analogous to those described in Patents EP-0 556 672 and U.S. Pat. No. 3,801,636 and in *J. Chem. Soc.*, (1927), 25, *Chem. Pharm. Bull.*, (1992), 1789-1792, *Aust. J. Chem.*, (1984), 1938-1950 and *J. O. C.*, (1980), 527.

The invention, according to another of its aspects, also has as subject-matter the compounds of general formula (V):

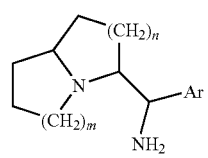

(V)

in which m and n each represent, independently of one another, the number 1 or 2, Ar represents a group chosen from the phenyl, naphth-1-yl, naphth-2-yl, pyridin-2-yl, pyridin-3-yl, pyridin-4-yl, furan-2-yl, furan-3-yl, thien-2-yl, thien-3-yl, thiazol-2-yl and oxazol-2-yl groups, it being possible for this group Ar optionally to be substituted by one or more substituents chosen from halogen atoms and $(C_1-C_6)$alkyl, $(C_3-C_7)$cycloalkyl, $(C_3-C_7)$cycloalkyl$(C_1-C_6)$alkyl, $(C_1-C_6)$alkoxy, $(C_3-C_7)$cycloalkyloxy, $(C_3-C_7)$cyclo-alkyl$(C_1-C_6)$alkyloxy, $(C_1-C_6)$alkylthio, $(C_3-C_7)$cycloalkylthio, $(C_3-C_7)$cycloalkyl-$(C_1-C_6)$alkylthio, mono- or polyfluoro$(C_1-C_6)$alkyl and mono- or polyfluoro$(C_1-C_6)$alkyloxy groups.

These compounds are of use as intermediates in the synthesis of the compounds of formula (I).

Among the compounds of general formula (V) which are a subject-matter of the invention, a first group of compounds is composed of the compounds for which:

m and n each represent, independently of one another, the number 1 or 2,

Ar represents a group chosen from the phenyl, pyridin-2-yl, pyridin-3-yl, pyridin-4-yl, thien-2-yl and thien-3-yl groups, it being possible for this group Ar optionally to be substituted by one or more substituents chosen from halogen atoms and $(C_1-C_6)$alkyl, $(C_3-C_7)$cycloalkyl, $(C_3-C_7)$cycloalkyl$(C_1-C_6)$alkyl, $(C_1-C_6)$alkoxy, $(C_3-C_7)$cycloalkyloxy, $(C_3-C_7)$cycloalkyl$(C_1-C_6)$alkyloxy, $(C_1-C_6)$alkylthio, $(C_3-C_7)$cycloalkylthio, $(C_3-C_7)$cyclo-alkyl$(C_1-C_6)$alkylthio, mono- or polyfluoro$(C_1-C_6)$alkyl and mono- or polyfluoro-$(C_1-C_6)$alkyloxy groups.

Among the compounds of general formula (V) which are a subject-matter of the invention, a second group of compounds is composed of the compounds for which:

Ar represents a group chosen from the phenyl, pyridin-3-yl and thien-3-yl groups, it being possible for this group Ar optionally to be substituted by one or more substituents chosen from halogen atoms, m and n being as defined above.

Among the compounds of general formula (V) which are a subject-matter of the invention, a third group of compounds is composed of the compounds for which:

m and n each represent, independently of one another, the number 1 or 2,

Ar represents a group chosen from the phenyl, pyridin-3-yl and thien-3-yl groups, it being possible for this group Ar optionally to be substituted by one or more halogen atoms.

Among the compounds of general formula (V), mention may in particular be made of the following compounds:

trans-threo/erythro-1-(octahydroindolizin-5-yl)-1-phenyl-methanamine;

trans-threo-1-(octahydroindolizin-3-yl)-1-phenylmethanamine;

cis-erythro-1-(octahydroindolizin-3-yl)-1-phenylmethanamine;

trans-threo/erythro-1-(octahydro-2H-quinolizin-4-yl)-1-phenylmethanamine;

trans-threo/erythro-1-(octahydro-2H-quinolizin-4-yl)-1-(4-fluorophenyl)methanamine;

trans-threo-1-(octahydro-2H-quinolizin-4-yl)-1-(pyridin-3-yl)methanamine;

trans-threo/cis-erythro-1-(octahydro-2H-quinolizin-4-yl)-1-(thien-3-yl)methanamine.

The examples which will follow illustrate the preparation of a few compounds of the invention. The elemental microanalyses, the IR and NMR spectra and chiral column HPLC confirm the structures and the enantiomeric purities of the compounds obtained.

The numbers shown in brackets in the titles of the examples correspond to those in the 1st column of the table given later.

EXAMPLE 1(Compounds No. 1 and 2)

trans-threo-2-Chloro-N-[(octahydroindolizin-5-yl)
phenylmethyl]-3-trifluoromethyl-benzamide hydrochloride 1:1 and trans-erythro-2-chloro-N-[(octahydroindolizin-5-yl)
phenylmethyl]-3-trifluoromethyl-benzamide hydrochloride 1:1

1.1 trans-threo/erythro-1-(octahydroindolizin-5-yl)-1-phenylmethanamine.

0.62 g (4 mmol) of bromobenzene in solution in 5 ml of anhydrous tetrahydrofuran is introduced, under an argon atmosphere, into a 50 ml round-bottomed flask equipped with a magnetic stirrer and then the medium is cooled to −75° C. 1.6 ml (4 mmol) of a 2.5M solution of butyllithium in tetrahydrofuran are added and the mixture is left stirring for 40 min. 0.3 g (2 mmol) of trans-octahydroindolizine-5-carbonitrile in solution of 5 ml of tetrahydrofuran is added at −75° C. and the mixture is allowed to return to ambient temperature over 3 h. Water and ethyl acetate are added and the aqueous phase is separated and extracted with ethyl acetate. The combined organic phases are dried over sodium sulphate and filtered, and the imine is concentrated under reduced pressure and taken up in a 50 ml round-bottomed flask with 10 ml of methanol. The mixture is cooled to −5° C. and 0.38 g (10 mmol) of sodium borohydride is slowly added. Stirring is continued while allowing the temperature of the mixture to return to ambient temperature over 12 h. The mixture is concentrated under reduced pressure and the residue is taken up in water and ethyl acetate. The phases are separated and the aqueous phase is extracted with ethyl acetate. After washing the combined organic phases, drying over sodium sulphate, filtering and evaporating, 0.5 g of product is obtained in the form of a yellow oil which is used as is in the following stage.

1.2. trans-threo-2-Chloro-N-[(octahydroindolizin-5-yl)phenylmethyl]-3-trifluoro-methylbenzamide hydrochloride 1:1 and trans-erythro-2-chloro-N-[(octahydro-indolizin-5-yl)phenylmethyl]-3-trifluoromethylbenzamide hydrochloride 1:1.

0.5 g (2.17 mmol) of 1-(octahydroindolizin-5-yl)-1-phenylmethanamine, 0.36 ml (2.6 mmol) of triethylamine and 0.63 g (2.6 mmol) of 2-chloro-3-trifluoromethylbenzoic acid chloride are successively introduced into 10 ml of dichloromethane in a 50 ml round-bottomed flask and the mixture is stirred at ambient temperature for 1 h.

The mixture is treated with water and extracted several times with dichloromethane. After washing the organic phases with water and then with a 1N aqueous sodium hydroxide solution, drying over magnesium sulphate, filtering and evaporating the solvent under reduced pressure, the residue is purified by chromatography on a column of silica gel, elution being carried out with a mixture of dichloromethane and methanol.

0.06 g and 0.130 g of products corresponding to the trans-threo and trans-erythro isomers are obtained in the form of a colorless oil.

These products are subsequently converted to hydrochlorides starting from a 0.1N solution of hydrochloric acid in propan-2-ol.

Finally, 0.039 g corresponding to the trans-threo isomer is isolated,

Melting point: 132-134° C.,
$^1$H NMR (200 MHz, CDCl$_3$): 0.75-2.00 (m, 12H), 2.6-2.9 (m, 2H), 5.00 (d, 1H), 7.1-7.5 (m, 7H), 7.8 (t, 2H);

and 0.017 g corresponding to the trans-erythro isomer is isolated,

Melting point: 132-134° C.,
$^1$H NMR (200 MHz, CDCl$_3$): 0.70-2.00 (m, 11H), 2.1-2.45 (m, 2H), 3.15-3.35 (m, 1H), 5.20 (s, 1H), 6.9 (s, 1H), 7.1-7.4 (m, 6H), 7.6-7.75 (m, 2H).

EXAMPLE 2(Compound No. 5)

trans-threo-2-Chloro-N-[(octahydroindolizin-3-yl)phenylmethyl]-3-trifluoromethyl-benzamide hydrochloride 1.1

2.1. trans-threo-1-(Octahydroindolizin-3-yl)-1-phenylmethanamine.

0.61 g (4.12 mmol) of trans-octahydroindolizine-3-carbonitrile, in solution in 25 ml of anhydrous tetrahydrofuran, is introduced, under an argon atmosphere, into a 100 ml round-bottomed flask equipped with a magnetic stirrer. The medium is cooled to −75° C., 6.22 ml (12.24 mmol) of a 2M solution of phenyllithium in dibutyl ether are added and the mixture is allowed to return, with stirring to ambient temperature over 5 h. 3 ml of methanol are added, then water and ethyl acetate are added and the aqueous phase is separated and extracted with ethyl acetate. The combined organic phases are dried over sodium sulphate and filtered, and the imine is concentrated under reduced pressure and taken up in a 50 ml round-bottomed flask with 25 ml of methanol. The mixture is cooled to −5° C. and 0.78 g (20.6 mmol) of sodium borohydride is slowly added. Stirring is continued while allowing the mixture to return to ambient temperature over 12 h. The mixture is concentrated under reduced pressure, the residue is taken up in water and ethyl acetate, the phases are separated and the aqueous phase is extracted with ethyl acetate. After washing the combined organic phases, drying over sodium sulphate, filtering and evaporating, 0.8 g of product is obtained in the form of a yellow oil which is used as is in the following stage.

2.2. trans-threo-2-Chloro-N-[(octahydroindolizin-3-yl)phenylmethyl]-3-trifluoromethyl-benzamide hydrochloride 1:1

0.4 g (1.77 mmol) of trans-threo-1-(octahydroindolizin-3-yl)-1-phenylmethanamine, 0.3 ml (2.1 mmol) of triethylamine and 0.57 g (2.35 mmol) of 2-chloro-3-trifluoromethylbenzoic acid chloride are successively introduced into 15 ml of dichloromethane in a 50 ml round-bottomed flask and the mixture is stirred at ambient temperature for 12 h.

It is treated with water and extracted several times with dichloromethane. After washing the organic phases with water and then with a 1N aqueous sodium hydroxide solution, drying over magnesium sulphate, filtering and evaporating the solvent under reduced pressure, the residue is purified by chromatography on a column of silica gel, elution being carried out with a mixture of dichloromethane and methanol.

0.35 g of product corresponding to the trans-threo isomer is obtained in the form of a colorless oil.

It is converted to the hydrochloride from a 0.1N solution of hydrochloric acid in propan-2-ol.

Finally, 0.28 g is isolated in the form of a white solid.
Melting point: 138-139° C.,
$^1$H NMR (200 MHz, CDCl$_3$): 1.0-1.9 (m, 10H), 2.9 (t, 1H), 3.05-3.25 (m, 2H), 3.5-3.6 (m, 1H), 5.20 (d, 1H), 7.3-7.5 (m, 6H), 7.8 (t, 2H).

EXAMPLE 3(Compound No. 11)

cis-erythro-2-Chloro-N-[(octahydroindolizin-3-yl)phenylmethyl]-3-trifluoromethyl-benzamide hydrochloride 1:1

3.1. cis-erythro-1-(octahydroindolizin-3-yl)-1-phenylmethanamine.

According to the protocol described in Example 1.1, starting from 0.61 g (4 mmol) of cis-octahydroindolizine-3-carbonitrile, 0.9 g of product is obtained in the form of a yellow oil which is used as is in the following stage.
$^1$H NMR (200 MHz, CDCl$_3$): 1.00-2.00 (m, 12H), 2.35-2.50 (m, 1H), 3.00-3.15 (m, 1H), 4.15 (d, 1H), 7.1-7.4 (m, 5H).

3.2. cis-erythro-2-Chloro-N-[(octahydroindolizin-3-yl)phenylmethyl]-3-trifluoromethyl-benzamide hydrochloride 1:1.

According to the protocol described in Example 2.2, starting from 0.47 g (2 mmol) of cis-erythro-1-(octahydroindolizin-3-yl)-1-phenylmethanamine and 0.58 g (2.4 mmol) of 2-chloro-3-trifluoromethylbenzoic acid chloride, 0.44 g is obtained in the form of a colorless oil corresponding to the cis-erythro isomer.

This product is subsequently converted to the hydrochloride from a 0.1N solution of hydrochloric acid in propan-2-ol.

Finally, 0.28 g is isolated in the form of a white solid.
Melting point: 138-139° C.,
$^1$H NMR (200 MHz, CDCl$_3$): 0.09-1.0 (m, 1H), 1.1-1.35 (m, 5H), 1.4-1.55 (m, 2H), 1.65-1.9 (m, 3H), 2.00-2.15 (m, 1H), 2.7-2.80 (m, 1H), 3.20-3.30 (m, 1H), 5.25 (t, 1H), 7.3-7.6 (m, 6H), 7.8-7.9 (m, 2H).

EXAMPLE 4(Compounds No. 14 and 21)

trans-threo-2-Chloro-N-[(octahydroquinolizin-4-yl)
phenylmethyl]-3-trifluoromethyl-benzamide hydrochloride 1:1 and trans-erythro-2-chloro-N-[(octahydroquinolizin-4-yl)
phenylmethyl]-3-trifluoromethyl-benzamide hydrochloride 1:1

4.1.  trans-threo/erythro-1-(octahydro-2H-quinolizin-4-yl)-1-phenylmethanamine.

0.29 g (1.77 mmol) of trans-octahydroquinolizine-4-carbonitrile, in solution in 10 ml of anhydrous tetrahydrofuran, is introduced, under an argon atmosphere, into a 50 ml round-bottomed flask equipped with a magnetic stirrer. The medium is cooled to −75° C., 2 ml (4 mmol) of a 2M solution of phenyllithium in cyclohexane/ethyl ether (70/30) are added and the mixture is allowed to return to −50° C. with stirring over 3 h. 1 ml of methanol is added, then water and ethyl acetate are added at 25° C. and the aqueous phase is separated and extracted with ethyl acetate. The combined organic phases are dried over sodium sulphate and filtered, and the imine is concentrated under reduced pressure and taken up in a 50 ml round-bottomed flask with 10 ml of methanol. The mixture is cooled to −5° C. and 0.33 g (8.85 mmol) of sodium borohydride is slowly added. Stirring is continued while allowing the mixture to return to ambient temperature over 12 h. The mixture is concentrated under reduced pressure and the residue is taken up in water and ethyl acetate. The phases are separated and the aqueous phase is extracted with ethyl acetate. After washing the combined organic phases, drying over sodium sulphate, filtering and evaporating, 0.18 g of product is obtained in the form of a yellow oil which is used as is in the following stage.

4.2.  trans-threo-2-Chloro-N-[(octahydroquinolizin-4-yl)phenylmethyl]-3-trifluoro-methylbenzamide hydrochloride 1:1 and trans-erythro-2-chloro-N-[(octahydroquinolizin-4-yl)phenylmethyl]-3-trifluoromethylbenzamide hydrochloride 1:1.

0.18 g (0.74 mmol) of trans-threo/erythro-1-(octahydro-2H-quinolizin-4-yl)-1-phenylmethanamine, 0.20 g (0.89 mmol) of 2-chloro-3-trifluoromethylbenzoic acid, 0.17 g (0.9 mmol) of 1-(3-dimethylaminopropyl)-3-ethylcarbodiimide hydrochloride (EDCI) and 0.045 g (0.37 mmol) of dimethylaminopyridine are successively introduced into 10 ml of dichloromethane in a 50 ml round-bottomed flask and the mixture is stirred at ambient temperature for 12 h.

It is treated with water and extracted several times with dichloromethane. After washing the organic phases with water and then with a 1N aqueous sodium hydroxide solution, drying over magnesium sulphate, filtering and evaporating the solvent under reduced pressure, the residue is purified by chromatography on a column of silica gel, elution being carried out with a mixture of dichloromethane and methanol.

0.13 g of compound corresponding to the trans-threo isomer and 0.024 g of compound corresponding to the trans-erythro isomer are obtained in the colorless oil form.

They are converted to hydrochlorides from a 0.1N solution of hydrochloric acid in propan-2-ol.

Finally, 0.13 g is isolated in the form of a white solid formed of trans-threo isomer:

Melting point: 161-163° C., $^1$H NMR (200 MHz, $C_5D_5N$): 1.2-2.0 (m, 10H), 2.15-2.35 (m, 2H), 3.2 (t, 1H), 3.65-3.8 (m, 1H), 3.85-4.0 (m, 2H), 6.30 (d, 1H), 7.3-7.6 (m, 6H), 7.8 (d, 2H);

and 0.014 g is isolated in the form of a white solid formed of trans-erythro isomer:

Melting point: 245-247° C., $^1$H NMR (200 MHz, $C_5D_5N$): 1.0-2.1 (m, 12H), 2.3-2.6 (m, 2H), 3.00 (d, 1H), 4.0 (d, 1H), 6.30 (d, 1H), 7.2-7.8 (m, 7H), 8.3 (d, 1H).

EXAMPLE 5(Compounds No. 26 and 27)

trans-threo-2-Chloro-N-[(4-fluorophenyl)(octahydroquinolizin-4-yl)methyl]-3-trifluoromethylbenzamide hydrochloride 1:1 and trans-erythro-2-chloro-N-[(4-fluorophenyl)(octahydroquinolizin-4-yl)methyl]-3-trifluoromethylbenzamide hydrochloride 1:1.

5.1.  trans-threo/erythro-1-(octahydro-2H-quinolizin-4-yl)-1-(4-fluorophenyl)-methanamine.

1.33 g (7.61 mmol) of 1-bromo-4-fluorobenzene, in solution in 10 ml of anhydrous ethyl ether, are introduced, under an argon atmosphere, into a 50 ml round-bottomed flask equipped with a magnetic stirrer and then the medium is cooled to −75° C. 3.35 ml (8.37 mmol) of a 2.5M solution of butyllithium in hexane are subsequently added and the mixture is allowed to return to −40° C. with stirring over 90 min. 0.5 g (3 mmol) of trans-octahydroquinolizine-4-carbonitrile, in solution in 10 ml of ethyl ether, is subsequently added at −75° C. and this temperature is maintained for 90 min. The mixture is allowed to return to 0° C. and 2 ml of methanol are added, then, at 25° C., water and ethyl acetate are added and the aqueous phase is separated and extracted with ethyl acetate. The combined organic phases are dried over sodium sulphate and filtered, and the imine is concentrated under reduced pressure in order to be taken up in a 50 ml round-bottomed flask with 20 ml of methanol. The mixture is cooled to −5° C. and 0.57 g (15.2 mmol) of sodium borohydride is slowly added. Stirring is continued while allowing the mixture to return to ambient temperature over 12 h. The mixture is concentrated under reduced pressure and the residue is taken up in water and ethyl acetate. The phases are separated and the aqueous phase is extracted with ethyl acetate. After washing the combined organic phases, drying with sodium sulphate, filtering and evaporating, 0.97 g of product is obtained in the form of a yellow oil which is used as is in the following stage.

5.2.  trans-threo-2-chloro-N-[(4-fluorophenyl)(octahydroquinolizin-4-yl)methyl]-3-tri-fluoromethylbenzamide hydrochloride 1:1 and trans-erythro-2-chloro-N-[(4-fluorophenyl)(octahydroquinolizin-4-yl)methyl]-3-trifluoromethylbenzamide hydrochloride 1:1.

0.4 g (1.52 mmol) of trans-threo/erythro-1-(octahydro-2H-quinolizin-4-yl)-1-(4-fluoro-phenyl)methanamine, 0.23 ml (1.8 mmol) of triethylamine and 0.4 g (1.67 mmol) of 2-chloro-3-trifluoromethylbenzoic acid chloride are successively introduced into 10 ml of dichloromethane in a 50 ml round-bottomed flask and the mixture is stirred at ambient temperature for 12 h.

The mixture is treated with water and extracted several times with dichloromethane. After washing the organic phases with water and then with a 1N aqueous sodium hydroxide solution, drying over magnesium sulphate, filtering and evaporating the solvent under reduced pressure, the residue is purified by chromatography on a column of silica gel, elution being carried out with a mixture of dichloromethane and methanol.

0.11 g of compound corresponding to the trans-threo isomer and 0.15 g of compound corresponding to the trans-erythro isomer are obtained in the colorless oil form.

These products are subsequently converted to hydrochlorides from a 0.1N solution of hydrochloric acid in propan-2-ol.

Finally, 0.082 g of trans-threo isomer is isolated in the form of a white solid:

Melting point: 176-178° C., $^1$H NMR (200 MHz, CDCl$_3$): 1.3-2.3 (m, 12H), 2.6-2.85 (m, 1H), 3.2 (t, 1H), 3.55-3.8 (m, 2H), 5.65 (t, 1H), 7.15 (t, 2H), 7.35 (t, 2H), 7.5 (t, 1H), 7.8 (d, 1H), 8.05 (d, 1H), 8.75 (d, 1H, NH);

and 0.095 g of trans-erythro isomer is isolated in the form of a white solid:

Melting point: 188-189° C., $^1$H NMR (200 MHz, CDCl$_3$): 1.1-2.6 (m, 12H), 2.7-3.2 (m, 3H), 3.95 (d, 1H), 5.80 (t, 1H), 7.15 (t, 2H), 7.35 (t, 2H), 7.5 (t, 1H), 7.8 (d, 1H), 7.95 (d, 1H), 9.3 (d, 1H, NH).

EXAMPLE 6(Compound No. 20)

trans-threo-2-Chloro-N-[(octahydroquinolizin-4-yl)(pyridin-3-yl)methyl]-3-trifluoromethyl-benzamide hydrochloride 1:1

6.1. trans-threo-1-(Octahydro-2H-quinolizin-4-yl)-1-(pyridin-3-yl)methanamine.

According to the protocol described in Example 5.1, starting from 0.8 g (5.32 mmol) of 3-bromopyridine and 0.35 g (2.13 mmol) of trans-octahydroquinolizine-4-carbonitrile, 0.57 g of product is obtained in the form of a brown oil which is used as is in the following stage.

6.2. trans-threo-2-Chloro-N-[(octahydroquinolizin-4-yl)(pyridin-3-yl)methyl]-3-tri-fluoromethylbenzamide hydrochloride 1:1.

According to the protocol described in Example 5.2, starting from 0.57 g (2.32 mmol) of trans-threo-1-(octahydro-2H-quinolizin-4-yl)-1-(pyridin-3-yl)methanamine and 0.62 g (2.55 mmol) of 2-chloro-3-trifluoromethylbenzoic acid chloride, 0.21 g of compound corresponding to the trans-threo isomer is obtained.

This product is subsequently converted to the hydrochloride from a 0.1N solution of hydrochloric acid in propan-2-ol.

Finally, 0.042 g of trans-threo isomer is isolated in the form of a white solid:

Melting point: 236-238° C.

$^1$H NMR (200 MHz, CDCl$_3$): 1.3-2.4 (m, 12H), 2.6-2.9 (m, 1H), 3.2 (t, 1H), 3.65-3.90 (m, 2H), 5.75 (t, 1H), 7.3-7.55 (m, 2H), 7.8 (t, 2H), 8.05 (d, 1H), 8.65 (d, 1H), 8.8 (s, 1H), 9.1 (d, 1H, NH).

EXAMPLE 7(Compounds No. 10 and 12)

trans-threo-2-Chloro-N-[(octahydroindolizin-3-yl)(thien-3-yl)methyl]-3-trifluoromethyl-benzamide hydrochloride 1:1 and cis-erythro-2-chloro-N-[(octahydroindolizin-3-yl)(thien-3-yl)methyl]-3-trifluoro-methylbenzamide hydrochloride 1:1

7.1. trans-threo/cis-erythro-1-(octahydro-2H-quinolizin-4-yl)-1-(thien-3-yl)methanamine.

According to the protocol described in Example 5.1, starting from 1.1 g (6.9 mmol) of 3-bromothiophene and 0.41 g (2.76 mmol) of a trans/cis chiral mixture of octahydro-indolizine-5-carbonitrile, 0.51 g of product is obtained in the form of a brown oil which is used as is in the following stage.

7.2. trans-threo-2-Chloro-N-[(octahydroindolizin-3-yl)(thien-3-yl)methyl]-3-trifluoro-methylbenzamide hydrochloride 1:1 and cis-erythro-2-chloro-N-[(octahydroindolizin-3-yl)(thien-3-yl)methyl]-3-trifluoromethylbenzamide hydrochloride 1:1.

According to the protocol described in Example 5.2, starting from 0.51 g (2.15 mmol) of trans-threo/cis-erythro-1-(octahydro-2H-quinolizin-4-yl)-1-(thien-3-yl)methanamine and 0.57 g (2.37 mmol) of 2-chloro-3-trifluoromethylbenzoic acid chloride, 0.25 g of compound corresponding to the trans-threo isomer and 0.14 g of compound corresponding to the cis-erythro isomer are obtained.

These products are subsequently converted to hydrochlorides from a 0.1N solution of hydrochloric acid in propan-2-ol.

Finally, 0.22 g of trans-threo isomer is isolated in the form of a white solid (RSS stereochemistry):

Melting point: 159-161° C.,

[α]$_D$=−55.2° (c=1.01, MeOH), $^1$H NMR (200 MHz, CDCl$_3$): 1.1-2.2 (m, 10H), 2.85 (t, 1H), 3.0-3.2 (m, 2H), 3.55-3.70 (m, 1H), 5.4 (t, 1H), 7.1 (d, 1H), 7.2-7.35 (m, 2H), 7.5 (t, 1H), 7.8 (t, 2H);

and 0.16 g of cis-erythro isomer is isolated in the form of a white solid (RSS stereochemistry):

Melting point: 170-172° C.,

[α]$_D$=+46.8° (c=1.02, MeOH), $^1$H NMR (200 MHz, CDCl$_3$): 1.1-1.9 (m, 10H), 2.0-2.2 (m, 2H), 2.75-2.9 (m, 1H), 3.25 (d, 1H), 5.4 (t, 1H), 7.1 (d, 1H), 7.2 (s, 1H), 7.35 (d, 1H), 7.5 (t, 1H), 7.8 (t, 2H).

The stereochemistry of the compounds is illustrated on the following page.

The chemical structures and the physical properties of a few compounds of the invention are illustrated in the following table.

In the "Ar" column, C$_6$H$_5$ denotes a phenyl group, z-X—C$_6$H$_4$ denotes a phenyl group substituted by X in the z position, C$_5$H$_4$N-3 denotes a pyridin-3-yl group and C$_4$H$_3$S-3 denotes a thien-3-yl group.

In the "Salt" column "-" denotes a compound in the base state and "HCl" denotes a hydrochloride.

In the "M.p. (° C.)" column, (d) denotes a melting point with decomposition.

In the "St." column, t-t denotes a trans-threo configuration, t-e denotes a trans-erythro configuration, c-e denotes a cis-erythro configuration and rac. denotes a racemate.

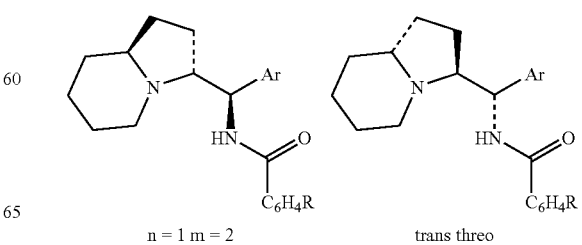

n = 1 m = 2          trans threo

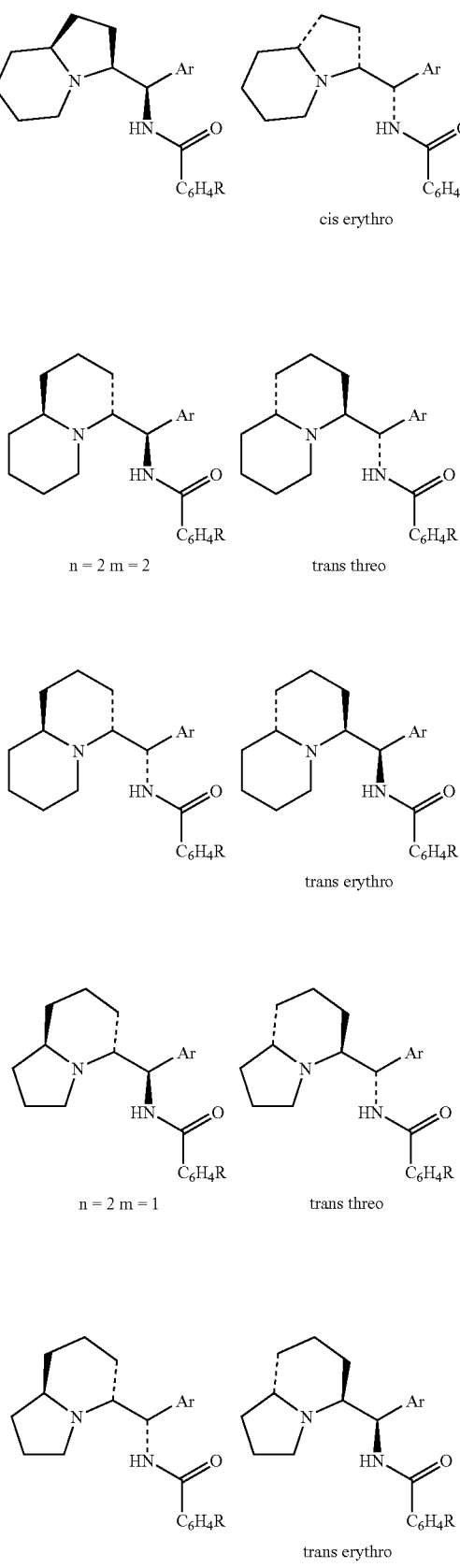

-continued n = 2 m = 2    trans threo trans erythro n = 2 m = 1    trans threo trans erythro

TABLE

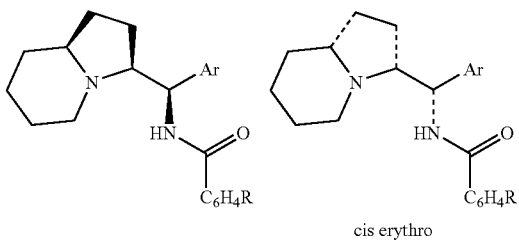

(I)

| No. | m | n | Ar | R | Salt | M.p. (° C.) | St. |
|---|---|---|---|---|---|---|---|
| 1 | 1 | 2 | $C_6H_5$ | 2-Cl, 3-$CF_3$ | HCl | 132-134 | t-t (rac.) |
| 2 | 1 | 2 | $C_6H_5$ | 2-Cl, 3-$CF_3$ | HCl | 132-134 | t-e (rac.) |
| 3 | 1 | 2 | $C_6H_5$ | 2,6-$(Cl)_2$, 3-$CF_3$ | HCl | 206-208 | t-t (rac.) |
| 4 | 1 | 2 | $C_6H_5$ | 2,6-$(Cl)_2$, 3-$CF_3$ | HCl | 254-256 | t-e (rac.) |
| 5 | 2 | 1 | $C_6H_5$ | 2-Cl, 3-$CF_3$ | HCl | 138-139 | t-t (rac.) |
| 6 | 2 | 1 | $C_6H_5$ | 2-Cl, 3-$CF_3$ | HCl | 240 (d) | t-t (RSS) |
| 7 | 2 | 1 | $C_6H_5$ | 2-$CH_3$, 3-$CF_3$ | HCl | 140-141 | t-t (rac.) |
| 8 | 2 | 1 | $C_6H_5$ | 2-$CH_3$, 3-$CF_3$ | HCl | 247-248 | c-e (rac.) |
| 9 | 2 | 1 | $C_5H_4N$-3 | 2-Cl, 3-$CF_3$ | HCl | 145-147 | t-t (RSS) |
| 10 | 2 | 1 | $C_4H_3S$-3 | 2-Cl, 3-$CF_3$ | HCl | 159-161 | t-t (RSS) |
| 11 | 2 | 1 | $C_6H_5$ | 2-Cl, 3-$CF_3$ | HCl | 138-139 | c-e (rac.) |
| 12 | 2 | 1 | $C_4H_3S$-3 | 2-Cl, 3-$CF_3$ | HCl | 170-172 | c-e (RRS) |
| 13 | 2 | 1 | $C_5H_4N$-3 | 2-Cl, 3-$CF_3$ | HCl | 131-133 | c-e (RRS) |
| 14 | 2 | 2 | $C_6H_5$ | 2-Cl, 3-$CF_3$ | HCl | 161-163 | t-t (rac.) |
| 15 | 2 | 2 | $C_6H_5$ | 2-Cl, 5-$CF_3$ | HCl | 142-144 | t-e (rac.) |
| 16 | 2 | 2 | $C_6H_5$ | 2,6-$(Cl)_2$, 3-$CF_3$ | HCl | 286-288 | t-t (rac.) |
| 17 | 2 | 2 | $C_6H_5$ | 2,6-$(Cl)_2$, 3-$CF_3$ | HCl | 205(d) | t-e (rac.) |
| 18 | 2 | 2 | $C_6H_5$ | 2-$CH_3$, 3-$CF_3$ | HCl | 166-167 | t-e (rac.) |
| 19 | 2 | 2 | 4-F—$C_6H_4$ | 2,6-$(Cl)_2$, 3-$CF_3$ | HCl | 289-291 | t-t (rac.) |
| 20 | 2 | 2 | $C_5H_4N$-3 | 2-Cl, 3-$CF_3$ | HCl | 236-238 | t-t (rac.) |
| 21 | 2 | 2 | $C_6H_5$ | 2-Cl, 3-$CF_3$ | HCl | 245-247 | t-e (rac.) |
| 22 | 2 | 2 | $C_6H_5$ | 2-Cl, 5-$CF_3$ | HCl | 255-257 | t-t (rac.) |
| 23 | 2 | 2 | $C_6H_5$ | 2-$CH_3$, 3-$CF_3$ | HCl | 141-143 | t-t (rac.) |
| 24 | 2 | 2 | $C_4H_3S$-3 | 2-Cl, 3-$CF_3$ | HCl | 157-159 | t-e (rac.) |
| 25 | 2 | 2 | $C_6H_5$ | 2-Cl, 3-$CH_3$ | HCl | 171-173 | t-t (rac.) |
| 26 | 2 | 2 | 4-F—$C_6H_4$ | 2-Cl, 3-$CF_3$ | HCl | 176-178 | t-t (rac.) |
| 27 | 2 | 2 | 4-F—$C_6H_4$ | 2-Cl, 3-$CF_3$ | HCl | 188-189 | t-e (rac.) |
| 28 | 2 | 2 | $C_6H_5$ | 2-$CH_3$, 3-$OCH_3$ | HCl | 224-226 | t-t (rac.) |
| 29 | 2 | 2 | $C_6H_5$ | 3-$OCF_3$ | HCl | 258-260 | t-t (rac.) |
| 30 | 2 | 2 | $C_6H_5$ | 3-$SF_5$ | HCl | 248-250 | t-t (rac.) |
| 31 | 1 | 1 | $C_6H_5$ | 2-Cl, 3-$CF_3$ | — | $MH^+$ = 423 | — |

The compounds of the invention have been subjected to a series of pharmacological trials which have demonstrated their advantage as substances possessing therapeutic activities.

Study of glycine transportation in SK-N-MC cells expressing the native human transporter GlyT1.

The uptake of [$^{14}$C]glycine is studied in SK-N-MC cells (human neuroepithelial cells) expressing the native human transporter GlyT1 by measuring the radioactivity incorporated in the presence or absence of the test compound. The cells are cultured as a monolayer for 48 hours in plates pretreated with 0.02% fibronectin. On the day of the experiment, the culture medium is removed and the cells are washed with Krebs-HEPES (4-(2-hydroxyethyl)piperazine-1-ethanesulphonic acid) buffer at pH 7.4. After preincubation for 10 minutes at 37° C. in the presence either of buffer (control batch) or of test compound at various concentrations or of 10 mM of glycine (determination of the non-specific uptake), 10 μM of [$^{14}$C]glycine (specific activity 112 mCi/mmol) are subsequently added. Incubation is continued for 10 min at 37° C. and the reaction is halted by washing twice with pH 7.4 Krebs-HEPES buffer. The radioactivity incorporated by the cells is then estimated after adding 100 μl of liquid scintillant and stirring for 1 h. Counting is carried out on a Microbeta Tri-Lux™ counter. The effectiveness of the compound is determined by the $IC_{50}$, the concentration of the compound which reduces by 50% the specific uptake of glycine, defined by the difference in radioactivity incorporated by the control batch and the batch which received the 10 mM glycine.

The compounds of the invention have, in this test, an $IC_{50}$ of the order of 0.001 to 0.20 μM.

| | |
|---|---|
| Compound 1 | $IC_{50}$ = 0.08 μM |
| Compound 2 | $IC_{50}$ = 0.023 μM |
| Compound 5 | $IC_{50}$ = 0.003 μM |

As shown by these results, the compounds of the invention exhibit a specific activity as inhibitors of the glycine transporters GlyT1.

The compounds according to the invention can thus be used in the preparation of medicaments, in particular of medicaments which are inhibitors of GlyT1 glycine transporters.

These results suggest that the compounds of the invention can be used for the treatment of behavioral disorders associated with dementia, psychoses, in particular schizophrenia (deficit form and productive form) and acute or chronic extrapyramidal symptoms induced by neuroleptics, for the treatment of various forms of anxiety, panic attacks, phobias, obsessive-compulsive disorders, for the treatment of various forms of depression, including is psychotic depression, for the treatment of disorders due to alcohol abuse or withdrawal, disorders of sexual behavior, eating disorders, for the treatment of migraine or in the treatment of primary generalized epilepsy, secondary generalized epilepsy, partial epilepsy with a simple or complex symptomatology, mixed forms and other epileptic syndromes, in complementing another anti-epileptic treatment or in monotherapy.

This is why another subject-matter of the present invention is pharmaceutical compositions comprising an effective dose of at least one compound according to the invention, in the form of the base or a pharmaceutically acceptable salt or solvate, as a mixture, if appropriate, with suitable excipients.

The said excipients are chosen according to the pharmaceutical form and the method of administration desired.

The pharmaceutical compositions according to the invention may thus be intended for oral, sublingual, subcutaneous, intramuscular, intravenous, topical, intratracheal, intranasal, transdermal, rectal or intraocular administration.

The unit administration forms can be, for example, tablets, gelatin capsules, granules, powders, solutions or suspensions to be taken orally or to be injected, transdermal patches or suppositories. Ointments, lotions and collyria can be envisaged for topical administration.

The said unit forms are dosed to allow a daily administration of 0.01 to 20 mg of active principle per kg of body weight, according to the pharmaceutical dosage form.

To prepare tablets, a pharmaceutical vehicle, which can be composed of diluents, such as, for example, lactose, microcrystalline cellulose or starch, and formulation adjuvants, such as binders (polyvinylpyrrolidone, hydroxypropylmethylcellulose, and the like), flow agents, such as silica, or lubricants, such as magnesium stearate, stearic acid, glyceryl tribehenate or sodium stearylfumarate, is added to the micronized or unmicronized active principle. Wetting or surface-active agents, such as sodium lauryl sulphate, can also be added.

The preparation techniques can be direct tableting, dry granulation, wet granulation or hot melt.

The tablets can be bare, coated with sugar, for example with sucrose, or coated with various polymers or other appropriate materials. They can be designed to make possible rapid, delayed or sustained release of the active principle by virtue of polymer matrices or of specific polymers used in the coating.

To prepare gelatin capsules, the active principle is mixed with dry pharmaceutical vehicles (simple mixing, dry or wet granulation, or hot melt) or liquid or semisolid pharmaceutical vehicles.

The gelatin capsules can be hard or soft and coated or uncoated with a thin film, so as to have a rapid, sustained or delayed activity (for example, for an enteric form).

A composition in the form of a syrup or an elixir or for administration in the form of drops can comprise the active principle in conjunction with a sweetener, preferably a calorie-free sweetener, methylparaben or propylparaben, as antiseptic, a flavor enhancer and a colorant.

The water-dispersible powders and granules can comprise the active principle as a mixture with dispersing agents or wetting agents, or dispersing agents, such as polyvinylpyrrolidone, as well as with sweeteners and flavor-correcting agents.

Recourse is had, for rectal administration, to suppositories prepared with binders which melt at the rectal temperature, for example cocoa butter or polyethylene glycols.

Use is made, for parental administration, of aqueous suspensions, isotonic saline solutions or injectable sterile solutions comprising pharmacologically compatible dispersing agents and/or wetting agents, for example propylene glycol or butylene glycol.

The active principle can also be formulated in the form of microcapsules, optionally with one or more vehicles or additives or else with a polymer matrix or with a cyclodextrin (transdermal patches or sustained release forms).

The topical compositions according to the invention comprise a medium compatible with the skin. They can be provided in particular in the form of aqueous, alcoholic or aqueous/alcoholic solutions, of gels, of water-in-oil or oil-in-water emulsions having the appearance of a cream or of a gel, of microemulsions or of aerosols or in the form of vesicular dispersions comprising ionic and/or nonionic lipids. These pharmaceutical dosage forms are prepared according to methods conventional in the fields under consideration.

Finally, the pharmaceutical compositions according to the invention can comprise, in addition to a compound of the general formula (I), other active principles which can be of use in the treatment of the disorders and diseases indicated above.

What is claimed is:

1. A compound, in the form of a pure enantiomer or of an erythro or threo diastereoisomer or of a mixture of such isomers, corresponding to formula (I):

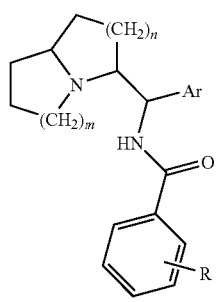

(I)

wherein:
m and n each represent, independently of one another, 1 or 2;

Ar represents a group chosen from phenyl, naphth-1-yl, naphth-2-yl, pyridin-2-yl, pyridin-3-yl, pyridin-4-yl, furan-2-yl, furan-3-yl, thien-2-yl, thien-3-yl, thiazol-2-yl and oxazol-2-yl groups, and wherein the Ar group is optionally substituted by one or more substituents selected from the group consisting of halogen, $(C_1-C_6)$ alkyl, $(C_3-C_7)$cycloalkyl, $(C_3-C_7)$cycloalkyl$(C_1-C_6)$ alkyl, $(C_1-C_6)$alkoxy, $(C_3-C_7)$cycloalkyloxy, $(C_3-C_7)$cycloalky $(C_1-C_6)$alkyloxy, $(C_1-C_6)$alkylthio, $(C_3-C_7)$ cycloalkylthio, $(C_3-C_7)$cycloalkyl$(C_1-C_6)$alkylthio, mono- or polyfluoro$(C_1-C_6)$alkyl and mono- or polyfluoro$(C_1-C_6)$alkyloxy groups; and R represents either a hydrogen atom or one or more substituents, identical to or different from one another, chosen from halogen atoms and mono- or polyfluoro$(C_1-C_6)$alkyl and mono- or polyfluoro$(C_1-C_6)$alkyloxy, linear $(C_1-C_6)$alkyl, branched or cyclic $(C_3-C_7)$alkyl, $(C_3-C_7)$cycloalkyl$(C_1-C_6)$alkyl, $(C_1-C_6)$alkoxy, $(C_3-C_7)$cycloalkyloxy, $(C_3-C_7)$cycloalkyl$(C_1-C_6)$alkyloxy, $(C_1-C_6)$alkylthio, cyano, amino, phenyl, acetyl, benzoyl, $(C_1-C_6)$alkylsulphonyl, carboxyl, $(C_1-C_6)$alkoxycarbonyl and pentafluorosulphanyl groups;

or an addition salt thereof with an acid.

2. The compound according to claim 1, wherein:
Ar represents a group chosen from phenyl, pyridin-2-yl, pyridin-3-yl, pyridin-4-yl, thien-2-yl and thien-3-yl groups, and wherein the Ar group is optionally substituted by one or more substituents, which are identical to or different from one another, chosen from halogen atoms and $(C_1-C_6)$alkyl, $(C_3-C_7)$cycloalkyl, $(C_3-C_7)$cycloalkyl$(C_1-C_6)$alkyl, $(C_1-C_6)$alkoxy, $(C_3-C_7)$cycloalkyloxy, $(C_3-C_7)$cycloalkyl$(C_1-C_6)$alkyloxy, $(C_1-C_6)$alkylthio, $(C_3-C_7)$cycloalkylthio, $(C_3-C_7)$cycloalkyl $(C_1-C_6)$ alkylthio, mono- or polyfluoro$(C_1-C_6)$alkyl and mono- or polyfluoro$(C_1-C_6)$alkyloxy groups; or
an addition salt thereof with an acid.

3. The compound according to claim 1, wherein:
Ar represents a group chosen from the phenyl, pyridin-3-yl and thien-3-yl groups, and wherein the Ar group is optionally substituted by one or more substituents, identical to or different from one another, chosen from halogen atoms; or
an addition salt thereof with an acid.

4. The compound according to claim 1, wherein:
R represents either a hydrogen atom or one or more substituents, which are identical to or different from one another, chosen from halogen atoms and mono- or polyfluoro$(C_1-C_6)$alkyl, mono- or polyfluoro$(C_1-C_6)$alkyloxy, linear $(C_1-C_6)$alkyl and pentafluorosulphanyl groups; or
an addition salt thereof with an acid.

5. The compound according to claim 2, wherein:
R represents either a hydrogen atom or one or more substituents, which are identical to or different from one another, chosen from halogen atoms and mono- or polyfluoro$(C_1-C_6)$alkyl, mono- or polyfluoro$(C_1-C_6)$alkyloxy, linear $(C_1-C_6)$alkyl and pentafluorosulphanyl groups; or
an addition salt thereof with an acid.

6. The compound according to claim 3, wherein:
R represents either a hydrogen atom or one or more substituents, which are identical to or different from one another, chosen from halogen atoms and mono- or polyfluoro$(C_1-C_6)$alkyl, mono- or polyfluoro$(C_1-C_6)$alkyloxy, linear $(C_1-C_6)$alkyl and pentafluorosulphanyl groups; or
an addition salt thereof with an acid.

7. The compound according to claim 1, wherein:
m and n each represent, independently of one another, 1 or 2;
Ar represents a group chosen from the phenyl, pyridin-3-yl and thien-3-yl groups, and wherein the Ar group is optionally substituted by one or more halogen atoms;
R represents either a hydrogen atom or one or more substituents, identical to or different from one another, chosen from chlorine and methyl, trifluoromethyl, trifluoromethoxy and pentafluorosulphanyl groups; or
an addition salt thereof with an acid.

8. The compound according to claim 1, which is selected from the group consisting of:
trans-threo-2-chloro-N-[(octahydroindolizin-5-yl)phenylmethyl]-3-trifluoromethylbenzamide hydrochloride;
trans-erythro-2-chloro-N-[(octahydroindolizin-5-yl)phenylmethyl]-3-trifluoromethylbenzamide hydrochloride;
trans-threo-2,6-dichloro-N-[(octahydroindolizin-5-yl) phenylmethyl]-3-trifluoromethylbenzamide hydrochloride;
trans-erythro-2,6-dichloro-N-[(octahydroindolizin-5-yl) phenylmethyl]-3-trifluoromethyl benzamide hydrochloride;
trans-threo-2-chloro-N-[(octahydroindolizin-3-yl)phenylmethyl]-3-trifluoromethylbenzamide hydrochloride;
2-chloro-N-[(S)-(3S,8aR)-(octahydroindolizin-3-yl) phenylmethyl]-3-thyrtrifluoromethylbenzamide hydrochloride;
trans-threo-2-methyl-N-[(octahydroindolizin-3-yl)phenylmethyl]-3-trifluoromethylbenzamide hydrochloride;
cis-erythro-2-methyl-N-[(octahydroindolizin-3-yl)phenylmethyl]-3-trifluoromethylbenzamide hydrochloride;
2-chloro-N-[(S)-(3S,8aR)-(octahydroindolizin-3-yl)(pyridin-3-yl)methyl]-3-trifluoromethyl-benzamide hydrochloride;
2-chloro-N-[(S)-(3S,8aR)-(octahydroindolizin-3-yl)(thiophen-3-yl)methyl]-3-trifluoro-methylbenzamide hydrochloride;
cis-erythro-2-chloro-N-[(octahydroindolizin-3-yl)phenylmethyl]-3-trifluoromethylbenzamide hydrochloride;
2-chloro-N-[(S)-(3R,8aR)-(octahydroindolizin-3-yl)(thiophen-3-yl)methyl]-3-trifluoro-methylbenzamide hydrochloride;
2-chloro-N-[(S)-(3R,8aR)-(octahydroindolizin-3-yl)(pyridin-3-yl)methyl]-3-trifluoro methylbenzamide hydrochloride;

trans-threo-2-chloro-N-[(octahydroquinolizin-4-yl)phenylmethyl]-3-trifluoromethylbenzamide hydrochloride;
trans-erythro-2-chloro-N-[(octahydroquinolizin-4-yl)phenylmethyl]-5-trifluoromethylbenzamide hydrochloride;
trans-threo-2,6-dichloro-N-[(octahydroquinolizin-4-yl)phenylmethyl]-3-trifluoromethyl benzamide hydrochloride;
trans-erythro-2,6-dichloro-N-[(octahydroquinolizin-4-yl)phenylmethyl]-3-trifluoromethyl benzamide hydrochloride;
trans-erythro-2-methyl-N-[(octahydroquinolizin-4-yl)phenylmethyl]-3-trifluoromethylbenzamide hydrochloride;
trans-threo-2,6-dichloro-N-[(4-fluorophenyl)(octahydroquinolizin-4-yl)methyl]-3trifluoromethylbenzamide hydrochloride;
trans-threo-2-chloro-N-[(octahydroquinolizin-4-yl)(pyridin-3-yl)methyl]-3-trifluoromethyl benzamide hydrochloride;
trans-erythro-2-chloro-N-[(octahydroquinolizin-4-yl)phenylmethyl]-3-trifluoromethylbenzamide hydrochloride;
trans-threo-2-chloro-N-[(octahydroquinolizin-4-yl)phenylmethyl]-5-trifluoromethylbenzamide hydrochloride;
trans-threo-2-methyl-N-[(octahydroquinolizin-4-yl)phenylmethyl]-3-trifluoromethylbenzamide hydrochloride;
trans-erythro-2-chloro-N-[(octahydroquinolizin-4-yl)(thiophen-3-yl)methyl]-3-trifluoro methylbenzamide hydrochloride;
trans-threo-2-chloro-3-methyl-N-[(octahydroquinolizin-4-yl)phenylmethyl]benzamide hydrochloride;
trans-threo-2-chloro-N-[(4-fluorophenyl)(octahydroquinolizin-4-yl)methyl]-3-trifluoro methylbenzamide hydrochloride;
trans-erythro-2-chloro-N-[(4-fluorophenyl)(octahydroquinolizin-4-yl)methyl]-3-trifluoro methylbenzamide hydrochloride;
trans-threo-2-chloro-3-methoxy-N-[(octahydroquinolizin-4-yl)phenylmethyl]benzamide hydrochloride;
trans-threo-N-[(octahydroquinolizin-4-yl)phenylmethyl]-3-trifluoromethoxybenzamide hydrochloride;
trans-threo-N-[(octahydroquinolizin-4-yl)phenylmethyl]-3-(pentafluorosulphanyl)benzamide hydrochloride; and
2-chloro-N-[(hexahydropyrrolizin-3-yl)phenylmethyl]benzamide hydrochloride.

9. A process for preparing the compound of formula (I) according to claim 1, comprising:
reacting a nitrile of formula (II):

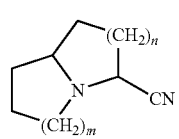

in which m and n are as defined in claim 1, with a lithiated derivative of formula Ar—Li, in which Ar is as defined in claim 1, in an ethereal solvent, between −90° C. and −30° C., in order to obtain an intermediate imine of formula (IV):

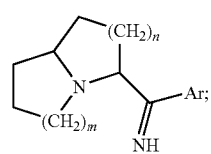

reducing the intermediate imine of formula (IV) to the primary amine of formula (V):

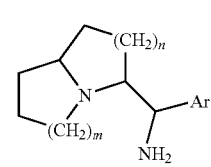

by a reducing agent, in a protic solvent, between 0° C. and ambient temperature; and
carrying out an amide coupling between the diamine of formula (V) and an activated acid or an acid chloride of general formula (VI):

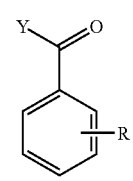

in which Y represents an activated OH group or a chlorine atom and R is as defined in claim 1.

10. A compound of formula (V):

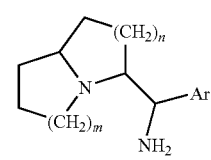

wherein:
m and n each represent, independently of one another, 1 or 2; and
Ar represents a group chosen from phenyl, naphth-1-yl, naphth-2-yl, pyridin-2-yl, pyridin-3-yl, pyridin-4-yl, furan-2-yl, furan-3-yl, thien-2-yl, thien-3-yl, thiazol-2-yl and oxazol-2-yl groups, the Ar group is optionally substituted by one or more substituents selected from the group consisting of halogen atoms and $(C_1$-$C_6)$alkyl, $(C_3$-$C_7)$cycloalkyl, $(C_3$-$C_7)$cycloalkyl$(C_1$-$C_6)$alkyl, $(C_1$-$C_6)$alkoxy, $(C_3$-$C_7)$cycloalkyloxy, $(C_3$-$C_7)$cycloalkyl$(C_1$-$C_6)$alkyloxy, $(C_1$-$C_6)$alkylthio, (C3-C7)cycloalkylthio, $(C_3$-$C_7)$cycloalkyl$(C_1$-$C_6)$alkylthio, mono- or polyfluoro$(C_1$-$C_6)$alkyl and mono- or polyfluoro$(C_1$-$C_6)$alkyloxy groups.

11. The compound according to claim 10, which is selected from the group consisting of:

trans-threo/erythro-1-(octahydroindolizin-5-yl)-1-phenylmethanamine;

trans-threo-1-(octahydroindolizin-3-yl)-1-phenylmethanamine;

cis-erythro-1-(octahydroindolizin-3-yl)-1-phenylmethanamine;

trans-threo/erythro-1-(octahydro-2H-quinolizin-4-yl)-1-phenylmethanamine;

trans-threo/erythro-1-(octahydro-2H-quinolizin-4-yl)-1-(4-fluorophenyl)methanamine;

trans-threo-1-(octahydro-2H-quinolizin-4-yl)-1-(pyridin-3-yl)methanamine; and trans-threo/cis-erythro-1-(octahydro-2H-quinolizin-4-yl)-1-(thien-3-yl)methanamine.

12. A pharmaceutical composition comprising a compound according to claim 1 in combination with an excipient.

13. A pharmaceutical composition comprising a compound according to claim 7 in combination with an excipient.

14. A pharmaceutical composition comprising a compound according to claim 8 in combination with an excipient.

* * * * *

UNITED STATES PATENT AND TRADEMARK OFFICE
CERTIFICATE OF CORRECTION

Page 1 of 1

PATENT NO.       : 7,776,880 B2
APPLICATION NO.  : 12/407276
DATED            : August 17, 2010
INVENTOR(S)      : Gihad Dargazanli et al.

It is certified that error appears in the above-identified patent and that said Letters Patent is hereby corrected as shown below:

In column 15, line 38, delete "including is" and insert -- including --, therefor.

In column 17, line 26-27, in claim 1, delete "cycloalky ($C_1$-$C_6$)alkyloxy" and insert -- cycloalkyl($C_1$-$C_6$)alkyloxy --, therefor.

In column 18, line 48, in claim 8, delete "thyrtrifluoromethylbenzamide" and insert -- trifluoromethylbenzamide --, therefor.

Signed and Sealed this
Nineteenth Day of July, 2011

David J. Kappos
*Director of the United States Patent and Trademark Office*